United States Patent
Tanaka et al.

(10) Patent No.: US 10,942,191 B2
(45) Date of Patent: Mar. 9, 2021

(54) SENSOR, DETECTION METHOD, DETECTION SYSTEM, AND DETECTION APPARATUS

(71) Applicants: KYOCERA CORPORATION, Kyoto (JP); KYUSHU UNIVERSITY, NATIONAL UNIVERSITY CORPORATION, Fukuoka (JP)

(72) Inventors: Hiroyasu Tanaka, Kyoto (JP); Hideharu Kurioka, Kyoto (JP); Shinsuke Sando, Fukuoka (JP)

(73) Assignees: KYUSHU UNIVERSITY, NATIONAL UNIVERSITY CORPORATION, Fukuoka (JP); KYOCERA CORPORATION, Kyoto (JP)

(*) Notice: Subject to any disclaimer, the term of this patent is extended or adjusted under 35 U.S.C. 154(b) by 751 days.

(21) Appl. No.: 14/894,894

(22) PCT Filed: Dec. 27, 2013

(86) PCT No.: PCT/JP2013/085212
§ 371 (c)(1),
(2) Date: Feb. 29, 2016

(87) PCT Pub. No.: WO2014/192196
PCT Pub. Date: Dec. 4, 2014

(65) Prior Publication Data
US 2016/0187358 A1 Jun. 30, 2016

(30) Foreign Application Priority Data
May 31, 2013 (JP) .............................. JP2013-115044

(51) Int. Cl.
*G01N 33/86* (2006.01)
*G01N 5/02* (2006.01)
(Continued)

(52) U.S. Cl.
CPC ............... *G01N 33/86* (2013.01); *C12Q 1/56* (2013.01); *G01N 5/02* (2013.01); *G01N 33/4905* (2013.01);
(Continued)

(58) Field of Classification Search
CPC combination set(s) only.
See application file for complete search history.

(56) References Cited

U.S. PATENT DOCUMENTS

| 6,352,630 B1 | 3/2002 | Frenkel et al. |
| 2010/0105079 A1 | 4/2010 | Warthoe |

(Continued)

FOREIGN PATENT DOCUMENTS

| JP | T 2005-502873 | 1/2005 |
| JP | 2010-529422 A | 8/2010 |
| WO | WO 2014/003075 | 1/2014 |

OTHER PUBLICATIONS

Päkkilä, Henna, et al. "Aptamer-directed lanthanide chelate self-assembly for rapid thrombin detection." Analyst 138.17 (2013): 5107-5112.*

(Continued)

*Primary Examiner* — Robert J Eom
(74) *Attorney, Agent, or Firm* — Duane Morris LLP

(57) ABSTRACT

There is provided a sensor and the like which can detect a first substance with high accuracy. A sensor for detecting whether an analyte contains a first substance, includes a base and a detection section including a second substance immobilized on a surface of the base. The second substance includes an amino acid, a bond which can be cleaved by a reaction with an enzyme, and a first compound which is bonded to the amino acid by the bond and includes a first group capable of bonding to other substances, and the analyte is configured to be introduced to the detection (Continued)

section by being contacted with a third substance which generates the enzyme by a reaction with the first substance.

15 Claims, 8 Drawing Sheets

(51) Int. Cl.
 C12Q 1/56 (2006.01)
 G01N 33/49 (2006.01)
 G01N 33/543 (2006.01)
(52) U.S. Cl.
 CPC ..... G01N 33/543 (2013.01); *G01N 2333/974* (2013.01)

(56) References Cited

U.S. PATENT DOCUMENTS

2010/0184106 A1* 7/2010 Qin ................ C07K 5/0812
 435/13
2011/0053285 A1 3/2011 Jeon et al.

OTHER PUBLICATIONS

Guhr, G., et al. "Novel sensor combining impedance spectroscopy and surface acoustic waves to detect blood coagulation time and hematocrit value." Sensors, 2011 IEEE. IEEE, 2011.*

Länge, Kerstin, Bastian E. Rapp, and Michael Rapp. "Surface acoustic wave biosensors: a review." Analytical and bioanalytical chemistry 391.5 (2008): 1509-1519.*

Basak, Sreela Pal, et al. "Application of electrical impedance spectroscopy and amperometry in polyaniline modified ammonia gas sensor." Synthetic metals 175 (2013): 127-133. (Year: 2013).*

Kim et al., "Determination of Protease Subsite Preference on SPOT Peptide Array by Fluorescence Quenching-based Assay", J. Pept. Sci., Apr. 30, 2012, vol. 18, p. 394-399.

Muramatsu, H., "Atsuden Soshi o Mochiiru Bio Sensing", Iden, 1989, vol. 43 No. 1, pp. 25-29.

Kondo et al., "Enzyme Biosensor Based on Surface Acoustic Wave Device", The Transactions of the Institute of Electronics Information and Communication Engineers C-I, 1995, vol. 78, No. 11, pp. 599-604.

Gray et al., Enzymatic Reactions on Immobilised Substrates, Chem. Soc. Rev., Apr. 2013, vol. 42, p. 6378-6405.

Official Action dated Jun. 6, 2017 in counterpart Japanese Patent Application No. 2015-519610 with Statement of Relevance of Non-English References.

Dominguez-Medina, S. et al., "In Situ Measurement of Bovine Serum Albumin Interaction with Gold Nanospheres", Langmuir, Apr. 2012, 28:9131-9139.

Kondoh et al., "Enzyme Biosensor Based on Surface Acoustic Wave Device", The Transactions of the Institute of Electronics Information and Communication Engineers C-I, 1995, vol. 78, No. 11, pp. 599-604.

* cited by examiner (a)

(b)

SENSOR, DETECTION METHOD, DETECTION SYSTEM, AND DETECTION APPARATUS

TECHNICAL FIELD

The present invention relates to a sensor, a detection method, a detection system, and a detection apparatus.

BACKGROUND ART

In the related art, for example, Patent Literature 1 discloses a system for measuring a blood clotting time. That is, in the system, a substrate having leaving groups is connected to one of two electrodes connected to an electric detection circuit, and the blood clotting time is measured using current generated in proportional to the number of leaving groups which are separated by the selective cleavage of a portion of the substrate and move to the other electrode.

CITATION LIST

Patent Literature

Patent Literature 1: Japanese Examined Patent Publication JP-B2 4662596

SUMMARY OF INVENTION

Technical Problem

However, according to the technology disclosed in Patent Literature 1, the substrate having the leaving groups is merely in contact with the electrode, and thus it may be difficult to accurately detect the number of leaving groups which are separated by the selective cleavage of a portion of the substrate.

For this reason, a method of accurately detecting a change associated with the aforementioned selective cleavage has been evaluated.

Solution to Problem

According to an embodiment of the invention, there is provided a sensor for detecting whether an analyte includes a first substance, the sensor including: a base; and a detection section comprising a second substance immobilized on a surface of the base, wherein the second substance includes an amino acid, a bond which can be cleaved by a reaction with an enzyme, and a first compound which is bonded to the amino acid by the bond and includes a first group capable of bonding to other substances, and the analyte is configured to be introduced to the detection section by being contacted with a third substance which generates the enzyme by a reaction with the first substance.

Advantageous Effects of Invention

In the sensor according to the embodiment of the invention, the second substance is immobilized on the surface of the base, and the first compound including the first group capable of bonding to other substances is bonded to the amino acid by the bond which can be cleaved by a reaction with the enzyme. Therefore, when a substance which is a bonding partner of the first compound is appropriately selected, it is possible to accurately detect the first substance based on the cleavage of the bond of the second substance which is caused by a reaction with the enzyme (due to an increase in signal intensity).

DESCRIPTION OF EMBODIMENTS

Figure 1:
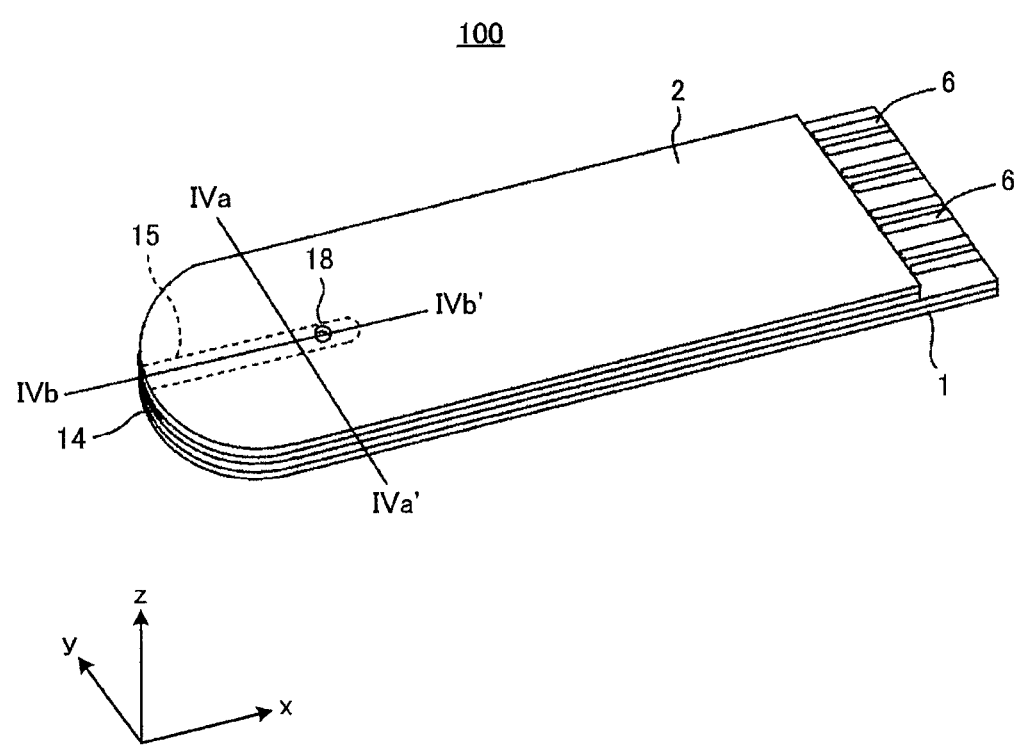
FIG. 1 is a perspective view of a sensor according to an embodiment of the invention.

Hereinafter, a sensor, a detection method, a detection system, and a detection apparatus according to an embodiment of the invention will be properly described in detail with reference to the accompanying drawings.

<Regarding Sensor>

A sensor according to the embodiment of the invention detects whether an analyte includes a first substance, and includes a base; and a detection section including a second substance immobilized on a surface of the base, wherein the second substance includes an amino acid; a bond which can be cleaved by a reaction with an enzyme; and a first compound which is bonded to the amino acid by the bond and includes a first group capable of bonding to other substances. The analyte is configured to be introduced into the detection section by being contacted with a third substance which generates an enzyme by a reaction with the first substance. The immobilization, referred to here, implies that two substances, for example, the second substance and the surface of the base is chemically bonded together (this implication applies to the description below). In the embodiment, examples of the analyte include blood and plasma.

Thus, it is possible to detect whether the analyte includes the first substance by introducing the analyte which comes into contact with the third substance to the detection section, and measuring whether the bond of the second substance is cleaved. More specifically, since the second substance is immobilized on the surface of the base, and the amino acid and the first compound including the first group capable of bonding to other substances are bonded to each other by the bond which can be cleaved by a reaction with an enzyme, when a substance which is a bonding partner of the first compound is appropriately selected, it is possible to accurately detect the first substance based on the cleavage of the bond of the second substance which is caused by a reaction with the enzyme.

Hereinafter, the first substance, which is a detection target, is also referred to as a "target substance". When a numerical range is defined using "to", unless specified, the numerical value range includes a lower limit value and an upper limit value. For example, in a numerical range of "300 to 500", unless specified, the lower limit is "300 or more", and the upper limit is "500 or less".

The sensor according to the embodiment is used in a detection method for detecting a state change in the surface of the base which occurs when the bond of the second substance is cleaved. Examples of the sensor include a measurement cell which is used for measurement by a surface plasmon resonance (SPR) apparatus, a surface acoustic wave (SAW) sensor, and a quartz crystal microbalance (QCM) quartz sensor. The detection method using these sensors will be described in detail later. A sensor with an element utilizing the SAW is preferably used in the following aspects. For example, since the sensor does not require an optical system compared to a sensor with an element utilizing the light, it is possible to realize a reduction in the size of the sensor. It is possible to detect a target substance in a very small amount of an analyte, for example, 2 to 100 uL of an analyte compared to the sensor with an element utilizing the light. The SAW sensor uses high-frequency signals as signals propagating through the element, and thus it is possible to select a necessary accuracy, and to increase test types or the width of a test range by selecting a certain frequency or a certain propagation path length.

Hereinafter, as an example of the structure of the sensor in the embodiment, a biosensor (hereinafter, which is also referred to as a sensor) 100 with an element utilizing the SAW will be described. The same reference signs will be assigned to the same configuration members in the drawings to be illustrated below. The size of each member, the distances between members, and the like are schematically illustrated, and may be different from actual ones. An upper side or a lower side of the sensor 100 may be defined by any direction. Hereinafter, for the sake of convenience, an xyz rectangular coordinate system is defined, and terms such as an upper surface and a lower surface are used with the upper side being positioned on a positive side in a z direction.

Figure 3:
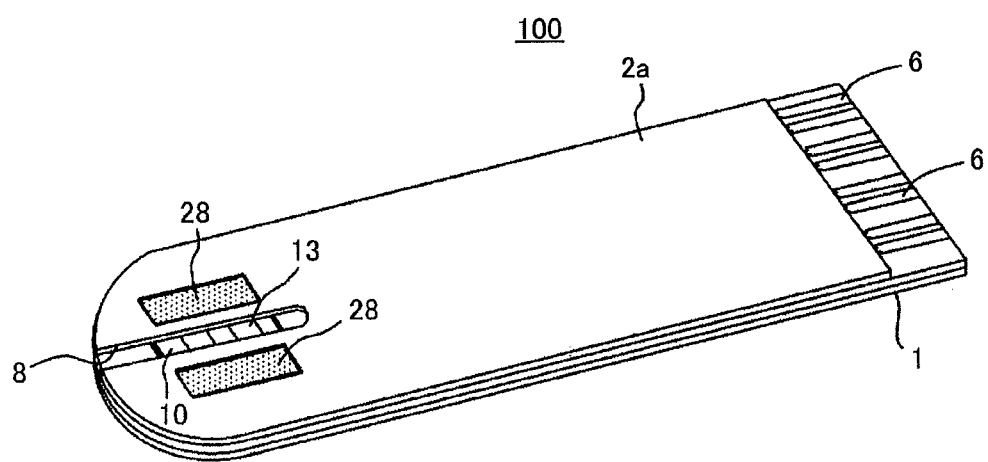
FIG. 3 is a perspective view of the sensor illustrated in FIG. 1, from which a fourth base is detached.

As illustrated in FIG. 3 and the like, the sensor 100 mainly is configured to include a first cover member 1; a second cover member 2; and a detection element 3.

In the embodiment, the sensor 100 includes the first cover member 1 with a base 10 being disposed on an upper surface thereof, and the second cover member 2 configured to be joined to the first cover member 1. In the sensor 100, the first cover member 1 and/or the second cover member 2 include an inflow port though which an analyte flows, and a groove portion extending from the inflow port at least to the surface of the base 10. For example, in the sensor 100, a recessed portion is provided in an upper surface of the first cover member 1, the base 10 is accommodated in the recessed portion, and the second cover member 2 includes the groove portion.

The sensor 100 includes a first IDT (InterDigital Transducer) electrode which is located on the surface of the base 10 and is configured to generate acoustic waves which propagates toward a detection section 13. The sensor 100 includes a second IDT electrode which is located on the surface of the base 10, and is configured to receive acoustic waves passing through the detection section 13.

The sensor 100 includes a first joining member which is configured to be joined to an upper surface of the base 10 and is configured to form a first vibration space above the first IDT electrode and tightly encloses the first IDT electrode in the first vibration space. The sensor 100 includes a second joining member which is configured to be joined to the upper surface of the base 10 and is configured to form a second vibration space above the second IDT electrode and tightly encloses the second IDT electrode in the second vibration space.

Hereinafter, each of the constituent elements will be described in detail.

[First Cover Member and Second Cover Member]

The first cover member 1 includes a first base 1a, and a second base 1b stacked on the first base 1a, and the second cover member 2 includes a third base 2a stacked on the second base 1b, and a fourth base 2b stacked on the third base 2a. The detection element 3 is an acoustic surface wave element, and mainly includes the base 10; a first IDT electrode 11; a second IDT electrode 12; and the detection section 13.

The first cover member 1 and the second cover member 2 are bonded together, and the detection element 3 is accommodated in an inside of the first cover member 1 and the second cover member 2 bonded together. As illustrated in the sectional view of FIG. 4, the first cover member 1 includes a recessed portion 5 in the upper surface thereof, and the detection element 3 is disposed in the recessed portion 5.

As illustrated in FIG. 1, the second cover member 2 includes an inflow port 14 which is an inlet for an analyte at one end portion in a longitudinal direction (x direction) thereof, and a groove portion 15 extending from the inflow port 14 toward a region directly above the detection element 3. In FIG. 1, the groove portion 15 is illustrated by the dotted line so as to show the position of the groove portion 15.

Figure 2:
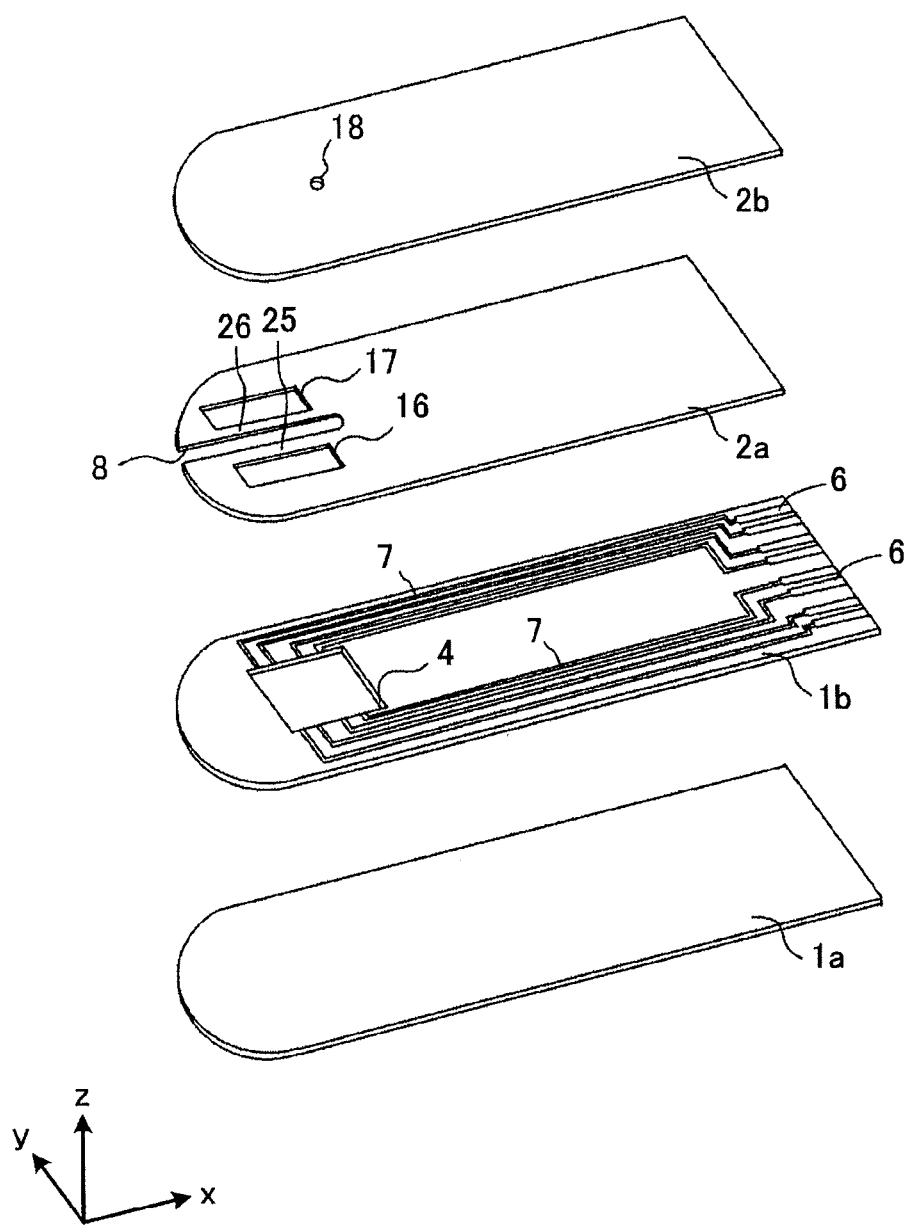
FIG. 2 is an exploded perspective view of a first cover member and a second cover member.

FIG. 2 illustrates an exploded perspective view of the first cover member 1 and the second cover member 2.

The first base 1a of the first cover member 1 has a flat-plate shape, and for example, the thickness thereof is 0.1 mm to 0.5 mm. The planar shape of the first base 1a is substantially a rectangular shape, and one end in the longitudinal direction of the first base 1a has an arc shape protruding toward the outside. For example, the length in the x direction of the first base 1a is 1 cm to 5 cm, and the length in a y direction thereof is 1 cm to 3 cm.

The second base 1b is bonded to an upper surface of the first base 1a. The second base 1b has a flat-plate frame shape, which is obtained by providing a recessed portion-formation through hole 4 in a flat plate, and the thickness thereof is 0.1 mm to 0.5 mm. The second base 1b has substantially the same exterior as that of the first base 1a in a plan view. The second base 1b has substantially the same lengths in the x direction and the y direction as those of the first base 1a.

The recessed portion 5 is formed in the first cover member 1 by joining the second base 1b provided with the recessed portion-formation through hole 4 to the flat plate-shaped first base 1a. That is, the upper surface of the first base 1a which is positioned on the inside of the recessed portion-formation through hole 4 is a bottom surface of the recessed portion 5, and an inner wall of the recessed portion-formation through hole 4 is an inner wall of the recessed portion 5.

A terminal 6, and a wiring 7 extending from the terminal 6 to the recessed portion-formation through hole 4 are formed on an upper surface of the second base 1b. The terminal 6 is formed in the other end portion in the x direction of the upper surface of the second base 1b. The portion of the upper surface, in which the terminal 6 is formed, is actually inserted into an external measurement apparatus (not illustrated) when the sensor 100 is inserted into the external measurement apparatus. The sensor 100 is electrically connected to the external measurement apparatus through the terminal 6. The terminal 6 is electrically connected to the detection element 3 through the wiring 7 and the like. A signal from the external measurement apparatus is inputted to the sensor 100 through the terminal 6, and a signal from the sensor 100 is outputted to the external measurement apparatus through the terminal 6.

The second cover member 2 is joined to an upper surface of the first cover member 1 composed of the first base 1a and the second base 1b. The second cover member 2 includes the third base 2a and the fourth base 2b.

The third base 2a is bonded to the upper surface of the second base 1b. The third base 2a has a flat plate shape, and for example, the thickness thereof is 0.1 mm to 0.5 mm. The planar shape of the third base 2a is substantially a rectangular shape, and similar to the first base 1a and the second base 1b, one end in the longitudinal direction of the third base 2a has an arc shape protruding toward the outside. For example, the length in the x direction of the third base 2a is slightly shorter than the length in the x direction of the second base 1b such that the terminal 6 formed on the second base 1b is exposed. For example, the length in the x direction is 0.8 mm to 4.8 cm. For example, the length in the y direction is 1 cm to 3 cm which is the same as those of the first base 1a and the second base 1b.

A cutaway 8 is formed in the third base 2a. The cutaway 8 is a portion which is cut away from an apex portion of one arc-shaped end of third base 2a toward the other end of the third base 2a in the x direction. The cutaway 8 is provided to form the groove portion 15. A first through hole 16 and a second through hole 17 are respectively formed on both adjacent sides of the cutaway 8 of the third base 2a in such a way as to penetrate through the third base 2a in a thickness direction thereof. When the third base 2a is stacked on the second base 1b, a connection portion between the detection element 3 and the wiring 7 is positioned on the inside of each of the first through hole 16 and the second through hole 17. A portion of the third base 2a between the first through hole 16 and the cutaway 8 serves as a first partition portion 25 partitioning a space which is formed by the groove portion 15 and the first through hole 16, which will be described later. A portion of the third base 2a between the second through hole 17 and the cutaway 8 serves as a second partition portion 26 partitioning a space which is formed by the groove portion 15 and the second through hole 17.

The fourth base 2b is bonded to an upper surface of the third base 2a. The fourth base 2b has a flat plate shape, and the thickness thereof is 0.1 mm to 0.5 mm. The fourth base 2b has substantially the same exterior as that of the third base 2a in a plan view. The fourth base 2b has substantially the same lengths in the x direction and the y direction as those of the third base 2a. The groove portion 15 is formed on a lower surface of the second cover member 2 by joining the fourth base 2b to the third base 2a in which the cutaway 8 is formed. That is, a lower surface of the fourth base 2b which is positioned on the inside of the cutaway 8 is a bottom surface of the groove portion 15, and an inner wall of the cutaway 8 is an inner wall of the groove portion 15. The groove portion 15 extends from the inflow port 14 at least to a region directly above the detection sections 13, and has a rectangular section.

A third through hole 18 is formed in the fourth base 2b in such a way as to penetrate through the fourth base 2b in a thickness direction thereof. When the fourth base 2b is stacked on the third base 2a, the third through hole 18 is positioned above an end portion of the cutaway 8. Accordingly, an end portion of the groove portion 15 is connected to the third through hole 18. The third through hole 18 is provided to discharge air and the like in the groove portion 15 to the outside.

The first base 1a, the second base 1b, the third base 2a, and the fourth base 2b are made of paper, plastic, celluloid, ceramics, or the like. All of these base bodies may be made of the same material. Since it is possible to set the thermal expansion coefficients of the base bodies to be substantially the same by making these base bodies of the same material, it is possible to suppress deformation caused by the difference in the thermal expansion coefficient between the base bodies. The detection section 13 may be coated with a biomaterial, and some biomaterials may be likely to deteriorate due to external light such as ultraviolet rays. In this case, the first cover member 1 and the second cover member 2 may be made of an opaque material having light shielding properties. In contrast, when external light causes almost no deterioration of the detection section 13, the second cover member 2 in which the groove portion 15 is formed may be made of a substantially transparent material. In this case, an operator can see the state of an analyte flowing through a flow path.

[Detection Element]

Figure 5:
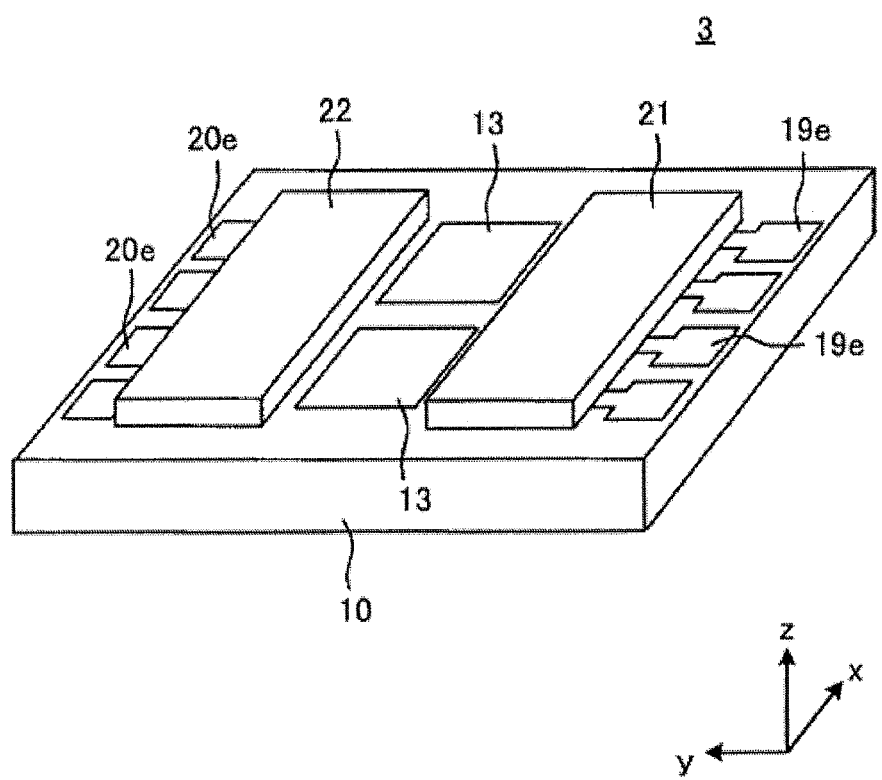
FIG. 5 is a perspective view of a detection element used in the sensor illustrated in FIG. 1.
Figure 6:
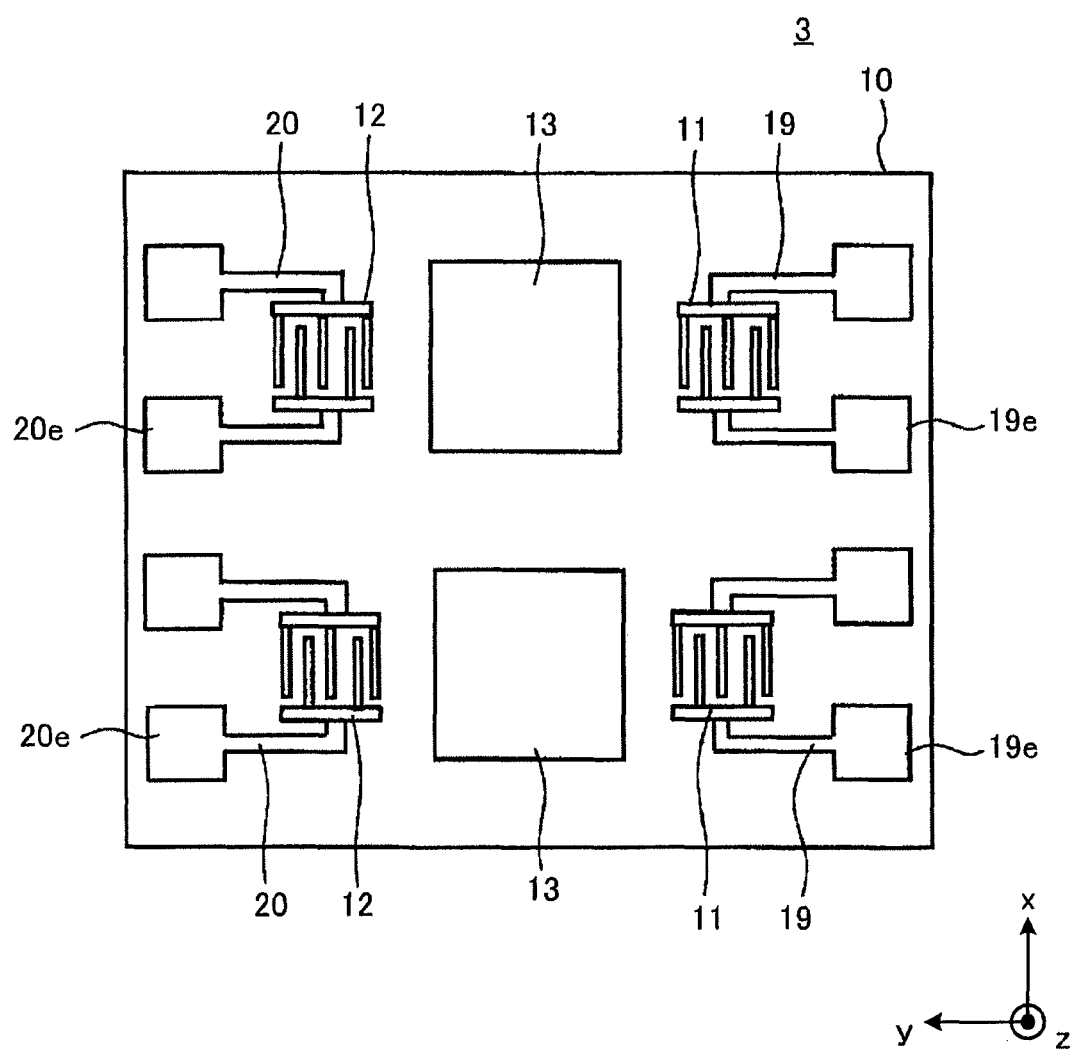
FIG. 6 is a plan view of the detection element illustrated in FIG. 5, from which a first joining member and a second joining member are detached.
Figure 7:
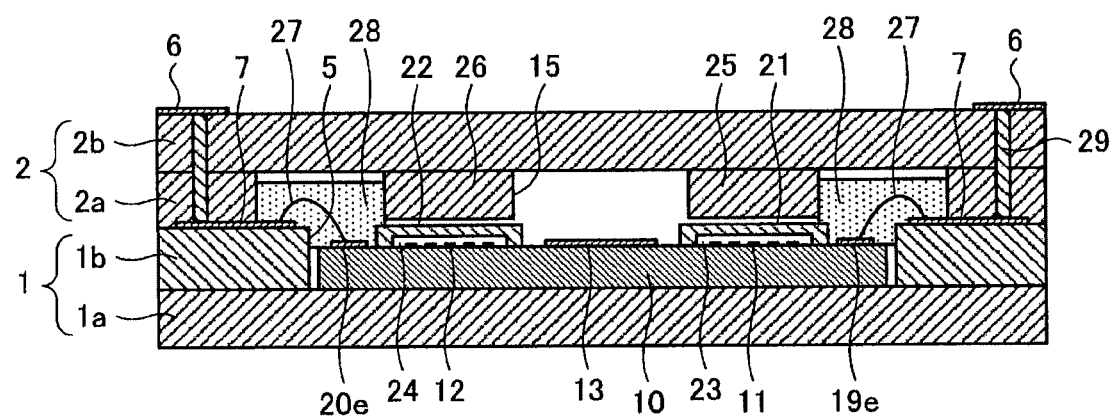
FIG. 7 is a sectional view illustrating a modified example of the sensor according to the embodiment of the invention.

FIG. 5 is a perspective view of the detection element 3, and FIG. 6 is a plan view of the detection element 3 from which a first joining member 21 and a second joining member 22 are detached.

The detection element 3 includes the base 10; the detection section 13 disposed on the upper surface of the base 10; the first IDT electrode 11; the second IDT electrode 12; a first extraction electrode 19; and a second extraction electrode 20.

(Base)

The base 10 is formed of a monocystalline substrate of a single crystal having piezoelectricity such as lithium tantalate ($LiTaO_3$) single crystal, lithium niobate ($LiNbO_3$) single crystal, or quartz. The planar shape and various dimensions of the base 10 may be appropriately set. By way of example, the thickness of the base 10 is 0.3 mm to 1 mm.

(IDT Electrode and Extraction Electrode)

As illustrated in FIG. 6, the first IDT electrode 11 includes a pair of comb-like electrodes. Each of the comb-like electrodes includes two bus bars facing each other, and a plurality of electrode fingers extending from one to the other of the bus bars. Each of the pair of comb-like electrodes is disposed in such a way that the plurality of electrodes fingers mesh with each other. The second IDT electrode 12 also has the same configuration as that of the first IDT electrode 11. The first IDT electrode 11 and the second IDT electrode 12 form a transversal IDT electrode.

It is possible to design a frequency characteristic based on the number of electrode fingers of each of the first IDT electrode 11 and the second IDT electrode 12, the distance between adjacent electrode fingers, the width of intersection between the electrode fingers, and the like which are parameters. Examples of a SAW excited by the IDT electrode include a Rayleigh wave, a Love wave, and a leaky wave. An elastic member for suppressing the reflection of the SAW may be provided in a region positioned on the outside in a propagation direction of a SAW of the first IDT electrode 11. For example, the frequency of the SAW can be set to a range from several megahertz (MHz) to several gigahertz (GHz). In particular, a range from several hundred MHz to 2 GHz is practical, and it is possible to realize a reduction in the size of the base 10, and consequently to realize a reduction in the size of the SAW sensor.

The first IDT electrode 11 generates a predetermined surface acoustic wave (SAW), and the second IDT electrode 12 receives the SAW generated by the first IDT electrode 11. The first IDT electrode 11 and the second IDT electrode 12 are disposed on the same straight line so that the second IDT electrode 12 can receive a SAW generated by the first IDT electrode 11. It is possible to design a frequency characteristic based on the number of electrode fingers of each of the first IDT electrode 11 and the second IDT electrode 12, the distance between adjacent electrode fingers, the width of intersection between the electrode fingers, and the like which are parameters. A SAW is excited in various vibration modes by the IDT electrode, and the detection element 3 uses the vibration mode of a transverse wave called an SH wave.

An elastic member for suppressing the reflection of the SAW may be provided in a region positioned on the outside in the propagation direction (y direction) of a SAW of the first IDT electrode 11 and the second IDT electrode 12. For example, the frequency of the SAW can be set to a range from several megahertz (MHz) to several gigahertz (GHz). In particular, a range from several hundred MHz to 2 GHz is practical, and it is possible to realize a reduction in the size of the detection element 3, and consequently to realize a reduction in the size of the sensor 100.

The first extraction electrode 19 is connected to the first IDT electrode 11. The first extraction electrode 19 is extracted from the first IDT electrode 11 to a side opposite to the detection section 13, and an end portion 19e of the first extraction electrode 19 is electrically connected to the wiring 7 provided on the first cover member 1. In addition, the second extraction electrode 20 is connected to the second IDT electrode 12. The second extraction electrode 20 is extracted from the second IDT electrode 12 to a side opposite to the detection section 13, and an end portion 20e of the second extraction electrode 20 is electrically connected to the wiring 7 provided on the second cover member 2.

The first IDT electrode 11, the second IDT electrode 12, the first extraction electrode 19, and the second extraction electrode 20 are made of aluminum, an alloy of aluminum and copper, or the like. These electrodes may have a multi-layer structure. When each of these electrodes has a multi-layer structure, for example, the first layer is made of titanium or chromium, and the second layer is made of aluminum or an aluminum alloy.

The first IDT electrode 11 and the second IDT electrode 12 are covered with a protective film (not illustrated). The protective film contributes to, for example, prevention of oxidation of the first IDT electrode 11 and the second IDT electrode 12. The protective film is made of silicon oxide, aluminum oxide, zinc oxide, titanium oxide, silicon nitride, silicon, or the like. The thickness of the protective film is approximately 1/10 (10 nm to 30 nm) of the thickness of each of the first IDT electrode 11 and the second IDT electrode 12. The protective film may be formed on the entire upper surface of the base 10 in such a way that the end portion 19e of the first extraction electrode 19 and the end portion 20e of the second extraction electrode 20 are exposed.

(Detection Section)

The detection section 13 is provided between the first IDT electrode 11 and the second IDT electrode 12. The detection section 13 includes, on the surface of the base 10, a second substance 200 including a bond 210 which can be cleaved by a reaction with an enzyme. The detection section 13 will be described in detail later.

When the first IDT electrode 11, the second IDT electrode 12, and the detection section 13 disposed along the y direction are deemed to be one set, two sets are provided in the sensor 100. In one of the two detection sections 13, the second substance 200 including the bond 210 which can be cleaved by a reaction with an enzyme may not be immobilized, and the one detection section 13 may be used as a reference.

(Joining Member)

As illustrated in FIG. 5, the first IDT electrode 11 may be covered with the first joining member 21. The first joining member 21 is located on the upper surface of the base 10, and a space is formed in an inner region which is surrounded by the base 10 and the first joining member 21. An inner space surrounded by the first joining member 21 when the first joining member 21 is mounted on the upper surface of the base 10, is defined as a first vibration space 23. The first IDT electrode 11 is tightly enclosed in the first vibration space 23. Accordingly, the first IDT electrode 11 is isolated from outside air and an analyte, and the first IDT electrode 11 can be protected. Since the first vibration space 23 is secured, it is possible to suppress deterioration of the characteristics of a SAW excited by the first IDT electrode 11.

Similarly, the second IDT electrode 12 may be covered with the second joining member 22. Similar to the first joining member 21, the second joining member 22 is located on the upper surface of the base 10, and as illustrated in FIG. 4(a), a space is formed on the inside of the second joining member 22. An inner space surrounded by the second joining member 22 when the second joining member 22 is mounted on the upper surface of the base 10, is defined as a second vibration space 24. The second IDT electrode 12 is tightly enclosed in the second vibration space 24. Accordingly, the second IDT electrode 12 is isolated from outside air and an analyte, and the second IDT electrode 12 can be protected. Since the second vibration space 24 is secured, it is possible to suppress deterioration of the characteristics of a SAW received by the second IDT electrode 12.

The vibration space may have a rectangular parallelepiped shape, a dome shape in a sectional view, an elliptical shape in a plan view, or an arbitrary shape confirming to the shape, the disposition, and the like of the IDT electrode.

The first joining member 21 includes an annular frame which is fixed to the upper surface of the base 10 so as to surround the two first IDT electrodes 11 disposed along the x direction, and a cover which is fixed to the frame so as to block an opening of the frame. It is possible to form such a structure by forming a resin film using a photosensitive resin material, and patterning the resin film by photolithography. The second joining member 22 can be also formed in the similar manner.

In the sensor 100, the two first IDT electrodes 11 are covered with one first joining member 21; however, the two first IDT electrodes 11 may be separately covered with the first joining members 21, respectively. In addition, the two first IDT electrodes 11 may be covered with one first joining member 21, and a partition may be provided between the two first IDT electrodes 11. Similarly, the two second IDT electrodes 12 may be separately covered with the second joining members 22, respectively. One second joining member 22 may be used, and a partition may be provided between the two second IDT electrodes 12.

[Regarding Detection of Analyte]

When the detection element 3 using a SAW performs detection of an analyte, first, a predetermined voltage is applied to the first IDT electrode 11 from the external measurement apparatus through the wiring 7, the first extraction electrode 19, and the like. At this time, a region of the surface of the base 10 where the first IDT electrode 11 is formed is excited, and a SAW having a predetermined frequency is generated. A portion of the generated SAW propagates toward the detection section 13, passes through the detection section 13, and then reaches the second IDT electrode 12.

When the analyte includes the first substance, the bond 210 of the second substance 200 of the detection section 13 is cleaved by an enzyme generated by the first substance, and thus the structure of the second substance 200 is changed, and weight of the detection section 13 is changed, which will be described later. As a result, the characteristics such as a phase of the SAW passing through a lower portion of the detection section 13 are changed. When the SAW with the changed characteristics reaches the second IDT electrode 12, the second IDT electrode 12 generates a voltage according to the reached SAW. This voltage is outputted to the outside through the second extraction electrode 20, the wiring 7, and the like, and is read by the external measurement apparatus. As a result, the nature and the compositions of the analyte can be examined.

[Regarding Introduction of Analyte into Detection Section, and Flow Path]

In the sensor 100 of the embodiment, a capillary phenomenon is used to guide (introduce) the analyte to the detection section 13.

Specifically, when the second cover member 2 is joined to the first cover member 1, the groove portion 15 formed on the lower surface of the second cover member 2 forms a capillary tube. It is possible to induce a capillary phenomenon in the capillary tube formed by the groove portion 15 by setting the width, the diameter, or the like of the groove portion 15 to a predetermined value taking the type of the analyte, the materials of the first cover member 1 and the second cover member 2, and the like into consideration. For example, the width (dimension in the y direction) of the groove portion 15 is 0.5 mm to 3 mm, and the depth (dimension in the z direction) is 0.1 mm to 0.5 mm. The groove portion 15 includes an extension portion 15e extending beyond the detection sections 13, and the third through hole 18 communicating with the extension portion 15e is formed in the second cover member 2. When the analyte flows into the flow path, air in the flow path is discharged to the outside through the third through hole 18.

Since the tube inducing such a capillary phenomenon is formed in a cover member composed of the first cover member 1 and the second cover member 2, when the analyte is contacted with the inflow port 14, the analyte is suctioned into the cover member through the groove portion 15 serving as a flow path. Since the sensor 100 includes a suction mechanism for the analyte, the sensor 100 can suction the analyte without the aid of a tool such as a pipette. Since a portion of the sensor 100 where the inflow port 14 is positioned is rounded, and the inflow port 14 is formed at the apex of the portion, it is easy to identify the inflow port 14.

Figure 4:
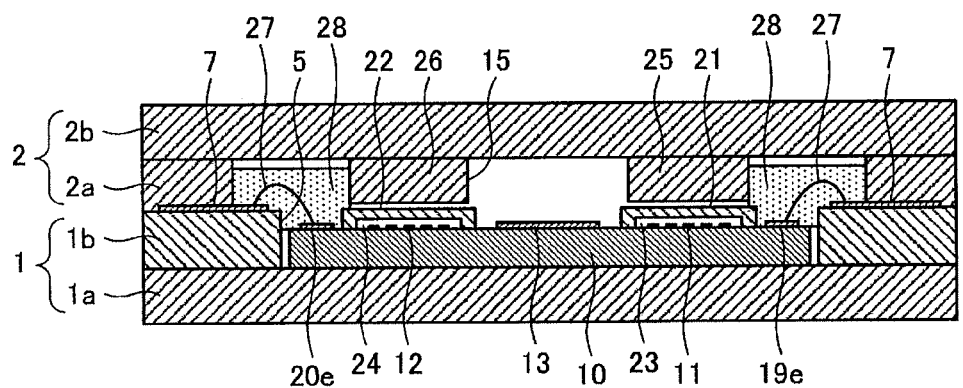
FIG. 4($a$) is a sectional view of the sensor taken along the line IVa-IVa' of FIG. 1, and FIG. 4($b$) is a sectional view of the sensor taken along the IVb-IVb' of FIG. 1.
Figure 4:
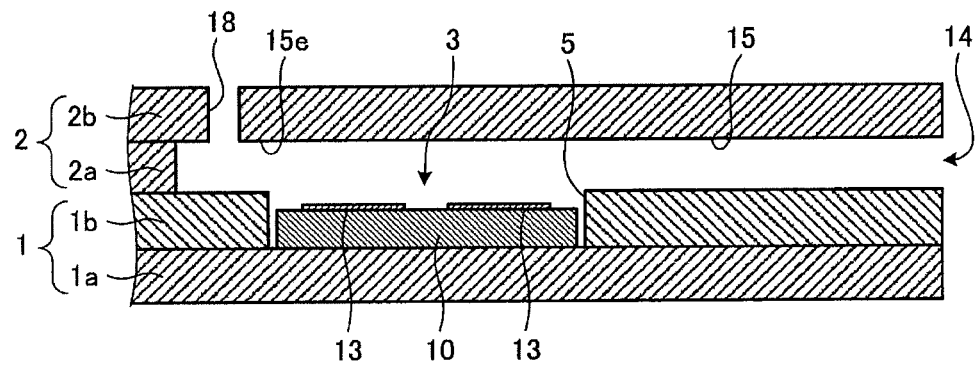

The flow path for the analyte formed by the groove portion 15 has a depth of approximately 0.3 mm, the thickness of the detection element 3 is approximately 0.3 mm, and the depth of the flow path is substantially the same as the thickness of the detection element 3. For this reason, when the detection element 3 is placed on the flow path directly, the flow path is blocked. As illustrated in FIG. 4, in the sensor 100, the recessed portion 5 is provided in the first cover member 1 on which the detection element 3 is mounted, and the detection element 3 is accommodated in the recessed portion 5. Therefore, the blocking of the flow path for the analyte is prevented. That is, by setting the depth of the recessed portion 5 to be substantially the same as the thickness of the detection element 3, and mounting the detection element 3 in the recessed portion 5, it is possible to secure the flow path formed by the groove portion 15.

FIG. 3 is a perspective view of the sensor 100 from which the fourth base 2b of the second cover member 2 is detached. According to this configuration, since the flow path for the analyte is secured, the analyte which has flowed into the flow path can be smoothly guided up to the detection section 13 by a capillary phenomenon.

As illustrated in FIG. 4, from the viewpoint that the flow path for the analyte is sufficiently secured, the height from the bottom surface of the recessed portion 5 to the upper surface of the base 10 may be the same as or be smaller than the depth of the recessed portion 5. For example, when the height from the bottom surface of the recessed portion 5 to the upper surface of the base 10 is set to be the same as the depth of the recessed portion 5, the bottom surface of the flow path and the detection section 13 can be positioned at substantially the same level when the inside of the groove portion 15 is seen from the inflow port 14. In the sensor 100, the thickness of the base 10 is smaller than the depth of the recessed portion 5, and the heights of the first joining member 21 and the second joining member 22 from the bottom surface of the recessed portion 5 is substantially the same as the depth of the recessed portion 5. When the heights of the first joining member 21 and the second joining member 22 from the bottom surface of the recessed portion 5 is greater than the depth of the recessed portion 5, the first partition portion 25 and the second partition portion 26 of the third base 2a are required to be processed in such a way that the thicknesses of the first partition portion 25 and the second partition portion 26 are smaller than other portions. In contrast, since the heights of the first joining member 21 and the second joining member 22 from the bottom surface of the recessed portion 5 is substantially the same as the depth of the recessed portion 5, this processing is not required, and productivity is improved.

The planar shape of the recessed portion 5 is similar to the planer shape of the base 10, and the recessed portion 5 is slightly greater than the base 10. More specifically, the size of the recessed portion 5 is set such that, when the base 10 is mounted in the recessed portion 5, a gap of approximately 100 μm is formed between a side surface of the base 10 and the inner wall of the recessed portion 5.

The detection element 3 is fixed to the bottom surface of the recessed portion 5 using a die bonding material including epoxy resin, polyimide resin, silicone resin, or the like as a main composition. The end portion 19e of the first extraction electrode 19 is electrically connected to the wiring 7 through a thin metal wire 27 made of Au or the like. The end portion 20e of the second extraction electrode 20 is connected to the wiring 7 in the same manner. Although the first extraction electrode 19 and the second extraction electrode 20 are connected to the wiring 7 using thin metal wire 27, it is not limited to this. For example, a conductive adhesive such as an Ag paste may be used.

Since voids are respectively provided at the connections between the first extraction electrode 19 and the wiring 7, and the second extraction electrode 20 and the wiring 7, when the second cover member 2 is bonded to the first cover member 1, damage of the thin metal wire 27 is suppressed. It is possible to simply form the voids by providing the first through hole 16 and the second through hole 17 in the third base 2a. Since the first partition portion 25 is present between the first through hole 16 and the groove portion 15, it is possible to suppress the flow of the analyte flowing through the groove portion 15 into the void formed by the first through hole 16. Accordingly, it is possible to suppress the occurrence of short-circuiting between a plurality of first extraction electrodes 19 which may be caused by the analyte. Similarly, since the second partition portion 26 is present between the second through hole 17 and the groove portion 15, it is possible to suppress the flow of the analyte flowing through the groove portion 15 into the void formed by the second through hole 17. Accordingly, it is possible to suppress the occurrence of short-circuiting between a plurality of second extraction electrodes 20 which may be caused by the analyte.

The first partition portion 25 is positioned above the first joining member 21, and the second partition portion 26 is positioned above the second joining member 22. Accordingly, more strictly speaking, the flow path for the analyte is formed by not only the groove portion 15 but also a groove portion-side side wall of the first joining member 21 and a groove portion-side side wall of the second joining member 22. From the viewpoint of preventing leakage of the analyte to the voids formed by the first through hole 16 and the second through hole 17, preferably, the first partition portion 25 is in contact with an upper surface of the first joining member 21, and the second partition portion 26 is in contact with an upper surface of the second joining member 22. In contrast, in the sensor 100, a gap is present between a lower surface of the first partition portion 25 and the upper surface of the first joining member 21, and a gap is present between a lower surface of the second partition portion 26 and the upper surface of the second joining member 22. For example, the gap is 10 μm to 60 μm. Since such a gap is provided, even though pressure is applied to this portion when an operator picks the sensor 100 with the fingers, the pressure can be absorbed by the gap, and the application of the pressure directly to the first joining member 21 and the second joining member 22 can be suppressed. As a result, large distortion of the first vibration space 23 and the second vibration space 24 can be suppressed. Since the analyte typically has a certain level of viscoelasticity, when the gap is set to 10 μm to 60 μm, the analyte is less prone to enter the gap, and the leakage of the analyte to the voids formed by the first through hole 16 and the second through hole 17 can be suppressed.

The width of the first partition portion 25 is greater than the width of the first vibration space 23. In other words, a side wall of the first partition portion 25 is positioned above the frame of the first joining member 21. Accordingly, even though the first partition portion 25 is contacted with the first joining member 21 due to external pressure, the first partition portion 25 is supported by the frame, and therefore deformation of the first joining member 21 can be suppressed. For the same reason, the width of the second partition portion 26 may be set to be greater than the width of the first vibration space 23.

The first extraction electrode 19, the second extraction electrode 20, the thin metal wires 27, and the wirings 7 which are positioned in the voids formed by the first through hole 16 and the second through hole 17, are covered with insulating members 28. Since the first extraction electrode 19, the second extraction electrode 20, the thin metal wires 27, and the wirings 7 are covered with the insulating members 28, corrosion of these electrodes and the like can be suppressed. Since the insulating members 28 are provided, even though the analyte enters the gap between the first partition portion 25 and the first joining member 21, or the gap between the second partition portion 26 and the second joining member 22, the analyte is blocked by the insulating members 28. Accordingly, short-circuiting between the extraction electrodes caused by the leakage of the analyte can be suppressed.

According to the sensor 100, the detection element 3 is accommodated in the recessed portion 5 of the first cover member 1, and thus it is possible to secure the flow path for the analyte from the inflow port 14 to the detection sections 13, and the analyte suctioned through the inflow port can flow to the detection sections 13 due to a capillary phenomenon or the like. That is, it is possible to provide the sensor 100 including the suction mechanism while using the thick detection element 3.

(Regarding Details of Detection Section of Sensor)

As described above, the detection section 13 includes the second substance 200 immobilized on the surface of the base 10.

The second substance 200 includes an amino acid; the bond 210 which can be cleaved by a reaction with an enzyme; and a first compound 201 which is bonded to the amino acid by the bond 210 and includes a first group 202 capable of bonding to other substances, which will be described later. The first compound 201 includes the first group 202 capable of bonding to other substances. Examples of the enzyme include thrombin.

The first substance is a substance which may be included in the analyte and detected by the sensor 100, the first substance generating an enzyme by a reaction with the third substance, and examples of the first substance include prothrombin. Examples of the third substance include thromboplastin. Examples of the enzyme include thrombin.

The detection section 13 may include a metal film, and the second substance 200 immobilized on the metal film. When the metal film is provided on the surface of the base 10, the metal film may be formed of arbitrary metal. The metal film may be made of gold, Ti, Cu, or the like, and preferably, is made of gold. Although the detection section 13 is located on the surface of the base 10, the detection section 13 may be located on the entire surface of the base 10, or on a portion of the surface of the base 10.

The detection section 13 can measure the prothrombin time of the analyte. In this case, examples of the first substance include blood clotting factors II, V, VII, and X. It is possible to determine the magnitude, for example, the density or the number of factors, of each of the blood clotting factors II, V, VII, and X by measuring the prothrombin time.

The third substance in measuring the prothrombin time is configured to alter into a substance capable of chemically reacting with the blood clotting factor X by reacting chemically with the blood clotting factor VII. Example of such a third substance include thromboplastin.

The prothrombin time can be measured in the following manner.

First, a calibration curve (for example, a relationship between a prothrombin time and a peak time) is acquired in advance using a reagent whose prothrombin time is known. The calibration curve may be prepared by acquiring and plotting peak times using a plurality of analytes whose prothrombin times are known according to the following technique.

Subsequently, the analyte comes into contact with the third substance (thromboplastin) such that an extrinsic clotting mechanism is activated. As a result, the first substance (prothrombin) is changed into an enzyme (thrombin).

A portion of the bond (amide bond) of the second substance immobilized on the surface of the base is cleaved by the enzyme (thrombin). Accordingly, the mass load of the second substance immobilized on a SAW propagation path is changed. The mass change is measured as time-dependency of a characteristic change (phase, amplitude, or the like) in a SAW.

For example, according to a technique of obtaining the prothrombin time from the measurement result, a first derivative of a curve for the characteristic change is taken, and a peak point is deemed to be time A. The prothrombin time corresponding to the time A can be obtained from the calibration curve which has been acquired in advance.

The detection section 13 may be one capable of measuring the activated partial thromboplastin time of the analyte. In this case, examples of the first substance include blood clotting factors II, V, VII, IX, X, XI, and XII.

The detection section 13 can determine the magnitude of each of the blood clotting factors II, V, VII, IX, X, XI, and XII by measuring the activated partial thromboplastin time.

The third substance in measuring the activated partial thromboplastin time is configured to alter into a substance capable of chemically reacting with the blood clotting factor XI by reacting chemically with the blood clotting factor XII. Examples of the third substance include ellagic acid.

Similar to the prothrombin time, the activated partial thromboplastin time can be measured in the following manner.

First, a calibration curve (for example, a relationship between an activated partial thromboplastin time and a peak time) is acquired in advance using a reagent whose activated partial thromboplastin time is known. The calibration curve may be prepared by acquiring and plotting peak times using a plurality of analytes whose activated partial thromboplastin times are known according to the following technique.

Subsequently, the analyte comes into contact with the third substance (ellagic acid) such that an intrinsic clotting mechanism is activated. As a result, the first substance (prothrombin) is changed into an enzyme (thrombin).

A portion of the bond (amide bond) of the second substance immobilized on the surface of the base is cleaved by the enzyme (thrombin). Accordingly, the mass load of the second substance immobilized on a SAW propagation path is changed. The mass change is measured as time-dependency of a characteristic change (phase, amplitude, or the like) in a SAW.

For example, according to a technique of obtaining the activated partial thromboplastin time from the measurement result, a first derivative of a curve for the characteristic change is taken, and a peak point is deemed to be time B. The activated partial thromboplastin time corresponding to the time B can be obtained from the calibration curve which has been acquired in advance.

As described above, the second substance 200 is immobilized on the surface of the base 10. The second substance 200 includes an amino acid; the bond 210 which can be cleaved by a reaction with an enzyme; and the first compound 201 which is bonded to the amino acid by the bond 210 and includes the first group 202 capable of bonding to other substances. The first compound 201 includes the first group 202 capable of bonding to other substances. Examples of the amino acid include alanine, valine, leucine, isoleucine, phenylalanine, tryptophan, methionine, proline, glycine, tyrosine, serine, threonine, cysteine, asparagine, glutamine, lysine, arginine, histidine, an aspartic acid, and a glutamic acid. Examples of the enzyme include thrombin.

It is preferable that the first compound 201 is an aromatic compound including a benzene ring. In this case, high-accuracy measurement can be performed within a relatively short time period. The first group 202 of the first compound 201 preferably includes at least one of an amino group and a carboxyl group. In this case, other substances can be bond thereto by an amide bond.

The second substance 200 preferably includes a second compound 203 including a second group 204 capable of bonding to other substances, the second compound 203 being positioned opposite to the first compound 201 with respect to the amino acid. In this case, various substances can be respectively bonded to both sides of the bond 210 which can be cleaved by the enzyme, and thus, it is possible to increase the accuracy of detection by optimizing the structure of the second substance for the detection section. Since it is possible to design the structure of the second substance 200 optimized for a detection method by selecting various compounds on one side of the second substance 200 with respect to the bond 210 while immobilizing the other side on the base 10, it is possible to improve accuracy in detecting the first substance.

For example, the second substance 200 is represented by Expression (1).

A-B-amino acid-C-D     Expression (1)

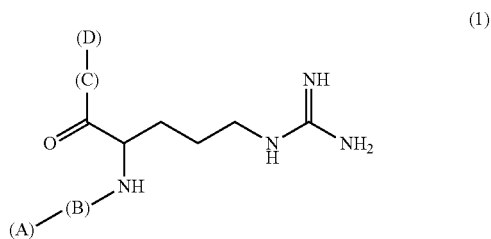

(1)

In the Expression, each of the A and the D includes at least one selected from a group consisting of Cys (cysteine), Lys (lysine), and biotin and polyethylene glycol derivatives, the B includes at least one selected from a group consisting of amino acids including Pro (proline) and Phe (phenylalanine) and a pipecolic acid, and the C includes an aromatic compound including phenylenediamine and aminobenzoic acid. For example, Arg (arginine) can be used as the amino acid.

In this example, the first compound 201 of the second substance 200 is (C), or (C) and (D) in the Expression. The first group 202 capable of bonding to other substances is a portion of (D) in the Expression. In this case, the amide bond between Arg (arginine) and (C) in the Expression can be cleaved by thrombin (enzyme). As a result, (C) and (D) in the Expression are separated from the second substance 200 immobilized on the surface of the base 10. As such, when a substance which is a bonding partner of the first compound 201 is appropriately selected, it is possible to improve accuracy in detecting the first substance based on the cleavage of the bond 210 of the second substance 200.

In Expression (1), pPDA (p-phenylenediamine) can be used as (C). In Expression (1), D-Phe-Pip can be used as B. D-Phe is phenylalanine of a D form, and Pip is a pipecolic acid.

The second substance 200 is preferably represented by Expression (2).

Expression (2) A-D-Phe-Pip-Arg-pPDA-D

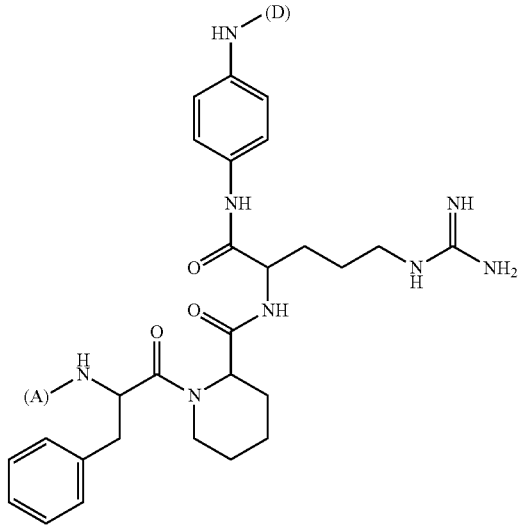

(2)

In this example, Arg (arginine) is used as the amino acid, the first compound 201 of the second substance 200 is pPDA (p-phenylenediamine), or pPDA (p-phenylenediamine) and (D) in the Expression. The first group 202 capable of bonding to other substances is a portion of (D) in the Expression. In this case, the amide bond between Arg (arginine) and pPDA (p-phenylenediamine) can be cleaved by thrombin (enzyme). As a result, pPDA (p-phenylenediamine) and (D) in the Expression are separated from the second substance 200 immobilized on the surface of the base 10. As such, by appropriately selecting a substance which is a bonding partner of the first compound 201, it is possible to improve accuracy in detecting the first substance based on the cleavage of the bond 210 of the second substance 200. Since pPDA (p-phenylenediamine) is an aromatic compound, it is possible to improve an efficiency of cleaving the amide bond between Arg (arginine) and pPDA (p-phenylenediamine) by thrombin which is an enzyme, and thus it is possible to measure the first substance within a shorter time period with high accuracy.

The second substance 200 preferably includes a nano particle 221 at a separation portion 220 which is separated from the detection section 13 when the bond 210 is cleaved. In this case, when the bond 210 of the second substance 200 is cleaved, the nano particle 221 is also separated from the detection section 13. As a result, it is possible to increase a state change in the surface of the base 10 compared to a case where the second substance 200 does not include the nano particle 221. That is, since it is possible to increase the amount of change in phase in the SAW sensor, it is possible to improve the accuracy of detection of the SAW sensor.

The nano particle 221 is formed using arbitrary one or more materials such as gold, silver, iron, aluminum, tin, white silver, chrome, nickel, latex, and the like by an arbitrary technique. The nano particle 221 preferably has a particle size of 100 nm or less.

The nano particle 221 is unlikely to non-specifically adsorb proteins and the like. When a gold nano particle is used, the surface of the nano particle 221 is preferably coated with SBA (Secondary Butyl Alcohol), BSA (Bovine Serum Albumin), lactoprotein, PEG (Poly Ethylene Glycol), or the like. It is known that a latex nano particle has non-specific adsorption smaller than that of a gold nano particle with a non-coated surface, and the latex nano particle is more preferable than a gold nano particle with a non-coated surface. The latex nano particle is preferably subjected to surface coating treatment.

(Regarding Method of Immobilization of Second Substance on Surface of Base)

Hereinafter, a technique of immobilization of the second substance 200 on the surface of the base 10 will be described.

An arbitrary technique may be used as the immobilization technique.

For example, immobilization may be made using strong affinity between streptavidin and biotin. In this case, streptavidin is immobilized on the detection section 13 in advance. In more detail, streptavidin is immobilized on the surface of the base in which a SAM (Self-Assembled Monolayer) which is formed of alkylthiol or the like is formed in advance so as to cover a surface (Au or the like) of the base 10 as much as possible. Biotin is immobilized on an end portion of the second substance 200 in advance, and a solution including the second substance 200 is prepared. Thereafter, the second substance 200 is immobilized by bringing the solution including the second substance 200 into contact with the region of the detection section 13. Thereafter, the detection section 13 may be cleaned using an arbitrary solution so as to remove the second substance 200 which is not immobilized on the detection section 13 and remains on the detection section 13. An example of the cleaning solution is NaOH. The cleaning solution is not limited to NaOH, and an arbitrary solution may be used as the cleaning solution. Alternatively, when the surface of the base 10 is made of gold, the second substance 200 is immobilized by immobilizing Cys (cysteine) on the end portion of the second substance 200 in advance, and bringing a solution including the second substance 200 into contact with the detection section 13.

As another example of the immobilization technique, a SAM is formed on the surface of the base 10 using well-known technology, and the SAM is modified with PEG such that the end of the modified SAM becomes COOH. Thereafter, the second substance 200 may be immobilized on the surface of the base 10 by causing the modified SAM to react with the second substance 200 including an amine group at the end of the second substance 200. In addition, Lys (lysine) is immobilized on the end portion of the second substance 200, and a SAM is modified with PEG such that the end of the modified SAM becomes COOH. Thereafter, the second substance 200 may be immobilized on the surface of the base 10 by causing the modified SAM to react with the second substance 200.

When the second substance 200 including a nano particle is used, an arbitrary nano particle may be immobilized on a compound whose bond 210 is cleaved by a reaction with thrombin, using the same technique as the technique of immobilizing the second substance 200 on the surface of the base 10. The compound on which the nano particle is immobilized may be used as the second substance 200.

A change in the propagation constant of a SAW is limited to a change in the extreme vicinity of the surface of the base 10. As a result, even though an unreacted substance not reacting with the analyte remains in the analyte existing on the base 10 or remains on the surface of the flow path, a process of removing the unreacted substance is not required.

It is possible to selectively detect an impact of the separation of the separation portion 220 of the second substance 200 by merely allowing the analyte to flow into the capillary flow path.

<Regarding Detection Method>

The detection method according to the embodiment of the invention includes preparing a sensor including a detection section including a second substance immobilized on a surface of a base, the second substance including a bond which can be cleaved by a reaction with an enzyme, and a first compound which is bonded to an amino acid by the bond and includes the first group capable of bonding to other substances; bringing an analyte, which is contacted with a third substance which generates the enzyme by a reaction with a first substance, into contact with the detection section of the sensor; and detecting whether the analyte includes the first substance by detecting cleavage of the bond of the second substance which is caused by the contact.

Hereinafter, the steps of the detection method will be sequentially described. Unless specified, the aforementioned descriptions regarding the sensor 100 are applicable hereinbelow.

Figure 8:
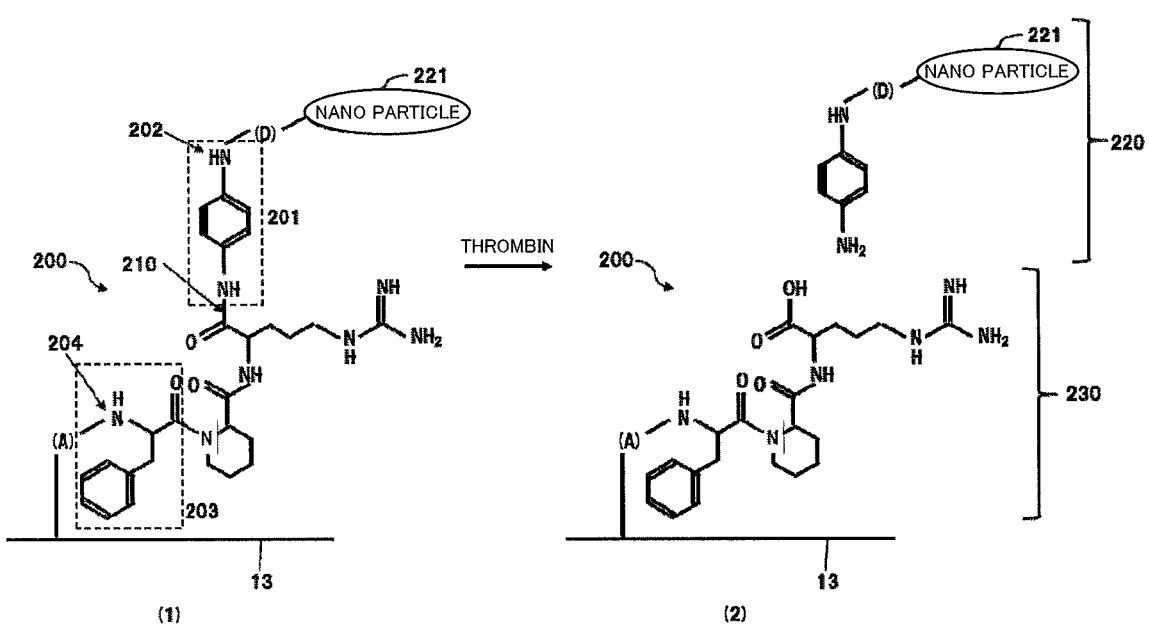
FIG. 8 shows views illustrating an example of the sensor according to the embodiment of the invention.

First, as illustrated in FIGS. 1 to 6 and 8, in particular, in FIGS. 6 and 8(1), carried out is a preparation step of preparing the sensor 100 including the detection section 13 including the second substance 200 immobilized on the surface of the base 10, the second substance 200 including an amino acid; the bond 210 which can be cleaved by a reaction with an enzyme; and the first compound 201 which is bonded to the amino acid by the bond 210 and includes the first group 202 capable of bonding to other substances.

For example, as illustrated in FIG. 8(1), the second substance 200 includes the nano particle 221 in addition to the configuration illustrated in Expression (2). The first group 202 is a portion of (D) in Expression (2), and the nano particle 221 as another substance is bonded to the first group 202.

Subsequently, as illustrated in FIG. 8, carried out is a contacting step of bringing the analyte which is contacted with the third substance which generates an enzyme by a reaction with the first substance, into contact with the detection section 13 of the sensor 100.

For example, the analyte is configured to be introduced into the detection section 13 of the sensor 100 by being contacted with the third substance which generates thrombin which is an example of the enzyme, and is contacted with the second substance 200. The second substance 200 is immobilized on the upper surface of the base 10, and includes the bond 210 which can be cleaved by a reaction with thrombin.

Specifically, the analyte which is contacted with the third substance by admixing the third substance with the analyte, may be directly contacted with the surface of the base 10 of the sensor 100 manually or otherwise. The analyte which is in contact with the third substance according to the same technique may flow into the flow path through the inflow port 14 of the sensor 100, and then to the detection section 13 from the inflow port 14 through the groove portion 15. As a result, the analyte comes into contact with the detection section 13. When the third substance is attached to the flow path of the sensor 100 in advance, the analyte may flow into the flow path through the inflow port 14, and then to the detection section 13 from the inflow port 14 through the groove portion 15 while coming into contact with the third substance attached to the flow path. As a result, the analyte comes into contact with the detection section 13.

Subsequently, as illustrated in FIG. 8(2), carried out is a detecting step of detecting whether the analyte includes the first substance by detecting the cleavage of the bond 210 of the second substance 200 in the contacting step.

For example, as illustrated in FIG. 8(2), it is possible to cleave the amide bond between Arg (arginine) which is one of amino acids and pPDA (p-phenylenediamine) by thrombin which is an enzyme. That is, the separation portion 220 including pPDA (p-phenylenediamine), (D), and the nano particle 221 in Expression (2) is separated from the second substance 200 immobilized on the base 10. As a result, molecular weight of the second substance 200 immobilized on the surface of the base 10 is changed, and the state of the surface of the base 10 is changed. In this case, a portion 230 of the immobilized second substance 200 other than the separation portion 220 which is positioned further away from the surface of the base 10 than the bond 210, remains on the surface of the base 10.

As such, by appropriately selecting a substance which is a bonding partner of the first compound 201, it is possible to accurately detect the first substance based on the cleavage of the bond 210 of the second substance 200 which is caused by a reaction with the enzyme. Since pPDA (p-phenylenediamine) is an aromatic compound, it is possible to improve an efficiency of cleaving the amide bond between Arg (arginine) and pPDA (p-phenylenediamine) by thrombin which is an enzyme, and thus it is possible to measure the first substance within a shorter time period with high accuracy.

As described above, it is possible to accurately detect the first substance by detecting a state change in the surface of the base 10 which occurs when the bond 210 of the second substance 200 is cleaved by a reaction with the enzyme. The change in the surface of the base 10 is due to the separation of the separation portion 220 of the second substance 200 from the detection section 13. For example, in a case where the bond 210 of the second substance 200 is cleaved by thrombin, the separation of the separation portion 220 from the second substance 200 occurs.

Examples of a state change in the surface of the base 10 include a mass change, an electric permittivity change, a viscoelasticity change, a propagation characteristics change, and a resonant frequency change which are induced by the separation of the separation portion 220 which occurs when the bond 210 of the second substance 200 immobilized on the surface of the base 10 is cleaved. For example, in a case where measurement is carried out using an SPR apparatus, when the bond 210 is cleaved and the separation portion 220 is separated, the mass or the electric permittivity of the surface of the base 10 is changed, and a change in SPR angle is induced by this change. In this case, a state change in the surface of the base 10 is a mass change or an electric permittivity change induced by the separation of the separation portion 220. The state change in the surface of the base 10 is detected by detecting a change in the SPR angle. When an SAW sensor is used, a propagation characteristics change is induced by a mass change or an electric permittivity change in the surface of the base 10. In this case, a state change in the surface of the base 10 is a mass change or an electric permittivity change induced by the separation of the separation portion 220, and is detected by detecting a propagation characteristics change. When a QCM measurement apparatus is used, a resonant frequency change is induced by a mass change in the surface of the base 10. In this case, a state change in the surface of the base 10 is a mass change induced by the separation of the separation portion 220, and is detected by detecting a resonant frequency change.

<Regarding Detection System and Detection Apparatus>

A detection system according to the embodiment of the invention includes the sensor 100 and a detection apparatus. Unless specified, the aforementioned descriptions regarding the sensor 100 are applicable hereinbelow.

The detection system according to the embodiment is a detection system for detecting whether an analyte includes a first substance, the detection system including a sensor including a detection section including a second substance immobilized on a surface of a base, the second substance including a bond which can be cleaved by a reaction with an enzyme, and a first compound which is bonded to an amino acid by the bond and includes a first group capable of bonding to other substances; and a detection apparatus configured to detect whether an analyte includes the first substance by detecting cleavage of the bond of the second substance caused by bringing the analyte, which is contacted with a third substance which generates an enzyme by a reaction with the first substance, into contact with the detection section of the sensor.

The detection apparatus according to the embodiment of the invention is an apparatus which executes an arbitrary detection process using the sensor 100. The detection apparatus is an SPR apparatus, a control apparatus of an SAW sensor, a QCM measurement apparatus, or the like, and preferably, a control apparatus of an SAW sensor. An SPR apparatus, a control apparatus of an SAW sensor, a QCM measurement apparatus can be arbitrarily used as the detection apparatus according to the embodiment insofar as these apparatuses are capable of carrying out measurement using the sensor 100.

Specifically, when the detection element 3 using an SAW carries out detection of an analyte, first, a predetermined voltage is applied to the detection element 3 through the first IDT electrode 11, the wiring 7, the first extraction electrode 19, and the like. At this time, a region of the surface of the base 10 where the first IDT electrode 11 is formed is excited, and a SAW having a predetermined frequency is generated. A portion of the generated SAW propagates toward the detection section 13, passes through the detection section 13, and then reaches the second IDT electrode 12.

When the analyte includes the first substance, the bond 210 of the second substance 200 constituting the detection section 13 is cleaved by an enzyme generated by the first substance, and thus the structure of the second substance 200 is changed and weight of the detection section 13 is changed. As a result, the characteristics such as a phase of the SAW passing through a lower portion of the detection section 13 are changed. When the SAW with the changed characteristics reaches the second IDT electrode 12, the second IDT electrode 12 generates a voltage according to the reached SAW. This voltage is outputted to the outside through the second extraction electrode 20, the wiring 7, and the like, and is read by the external measurement apparatus. As a result, the nature and the compositions of the analyte can be examined.

The detection apparatus and the detection system of the sensor 100 detect a change induced by the separation of the separation portion 220 of the second substance 200, rather than the first substance per se. In consideration of this, the detection apparatus may execute a conversion process of converting a detection result from the separation portion of the second substance 200 and the like into a result of detecting the first substance. For example, when molecular weight of the first substance and molecular weight of a signal substance are known, and a result indicating "that "x" grams (g) (or "mol") of the separation portion 220 is present" is obtained, this result may be converted into a result indicating "that "y" grams (g) (or "mol") of the first substance is present".

The invention is not limited to the embodiment, and may be realized in various forms.

For example, an example of using an acoustic surface wave element as the detection element 3 according to the aforementioned embodiment has been described. Instead, a detection element 3 including an optical waveguide or the like formed so as to cause surface plasmon resonance, may be used. In this case, for example, a change in the refractive index of light by the detection section is read. Besides, it is also possible to use a detection element 3 including an oscillator formed on a piezoelectric substrate such as quartz. In this case, for example, a change in the oscillating frequency of the oscillator is read.

Plural types of devices as the detection elements 3 may be provided on one base 10. For example, an enzyme electrode used in an enzyme electrode method may be provided adjacent to the SAW element. In this case, measurement by an enzyme method can be carried out in addition to immunization using an antibody or an aptamer, and it is possible to increase the number of items which can be tested at once.

In the aforementioned embodiment, an example of providing one detection element 3 has been described. However, a plurality of detection elements 3 may be provided. In this case, the recessed portion 5 may be provided for each of the detection elements 3, or a long recessed portion 5 may be formed so that all of the detection elements 3 can be accommodated therein.

In a case where a metal film is not required when the detection section 13 is formed by immobilizing the second substance 200 on the upper surface of the base 10, the metal film may not be used. In other words, the detection section 13 may be formed by immobilizing the second substance 200 on the region between the first IDT electrode 11 and the second IDT electrode 12 on the surface of the base (piezoelectric substrate) 10 without the metal film.

In the aforementioned embodiment, an example in which the first cover member 1 is formed by the first base 1a and the second base 1b, and the second cover member 2 is formed by the third base 2a and the fourth base 2b, has been described. However, the invention is not limited to this configuration, and for example, the first cover member 1 including the first base 1a and the second base 1b integrally formed may be used.

The groove portion 15 may be provided in either the first cover member 1 or the second cover member 2, or may be provided in both the first cover member 1 and the second cover member 2. For example, a flow path may be formed by respectively providing grooves on both the first cover member 1 and the second cover member 2, or a flow path may be formed by providing a groove on one side of the first cover member 1 and the second cover member 2.

In the aforementioned embodiment, an example in which the base 10 is provided on the first cover member 1, and the first cover member 1 and the second cover member 2 are joined together, has been described. However, the invention is not limited to this configuration. For example, a flow path may be formed by directly joining a cover portion to the base 10.

The base 10 may undergo a process of suppressing non-specific adsorption of proteins or the like to the base 10. For example, the surface of the base 10 is preferably coated with BSA (bovine serum albumin), PEG (Poly Ethylene Glycol), or the like. As a result, it is possible to measure a signal associated with the cleavage of the bond 210 of the second substance 200 while suppressing the impact of non-specific adsorption of proteins or the like on the signal.

Since an SAW detection circuit has the same circuit configuration as that adopted in communication apparatuses of various wireless terminals or tablet terminals, an SAW sensor can be simply connected to electronic equipment such as wireless terminal or tablet terminals.

As described above, the third substance to be contacted with an analyte may be attached to an arbitrary location in the sensor 100, and the analyte passes through a flow path such that the analyte may come into contact with the third substance. The third substance to be contacted with an analyte may be dissolved in the analyte before the analyte flows through the flow path of the sensor 100. When the third substance is attached to the sensor 100 in advance, the third substance is preferably attached to the groove portion rather than on the base 10. For example, the third substance may be attached to the ceiling of the flow path which faces the detection section 13 of the base 10, or the third substance may be attached to an arbitrary region that forms an inner flow path of a cover member on which the base 10 is mounted. The third substance is preferably attached to the vicinity of an SAW. In this case, since detection by the SAW can be carried out in a short time period after the analyte comes into contact with and reacts with the third substance, it is possible to suppress the occurrence of errors induced by the analyte, and to improve the accuracy of detection.

REFERENCE SIGNS LIST

1: First cover member
1a: First base
1b: Second base
2: Second cover member
2a: Third base
2b: Fourth base
3: Detection element
4: Recessed portion-formation through hole
5: Recessed portion
8: Cutaway
10: Base
11: First IDT electrode
12: Second IDT electrode
13: Detection section
14: Inflow port
15: Groove portion
16: First through hole
17: Second through hole
18: Third through hole
19: First extraction electrode
20: Second extraction electrode
21: First joining member
22: Second joining member
23: First vibration space
24: Second vibration space
25: First partition portion
26: Second partition portion
27: Thin metal wire
28: Insulating member
100: Biosensor (Sensor)
200: Second substance
201: First compound
202: First group
203: Second compound
204: Second group
210: Bond
220: Separation portion
221: Nano particle

The invention claimed is:

1. A sensor for detecting whether an analyte contains a first substance, the sensor comprising:
a base comprising a substrate having piezoelectricity; and
a detection section comprising a second substance immobilized on a surface of the substrate;
a first IDT (Inter Digital Transducer) electrode which is located on the surface substrate, and is configured to generate an acoustic wave which propagate toward the detection section;
a second IDT electrode which is located on the surface of the substrate, and is configured to receive the acoustic wave which passes through the detection section, wherein the detection section and the second substance are located on the surface of the substrate between the first and second IDT electrode, and the second substance includes
an amino acid,
a bond which can be cleaved by a reaction with an enzyme, and
a first compound which is bonded to the amino acid by the bond and includes a first group capable of bonding to other substances, and
the analyte is configured to be introduced to the detection section by being contacted with a third substance which generates the enzyme by a reaction with the first substance, wherein a weight of the detection section is changed by cleaving the bond, thereby changing a phase of the acoustic wave passing through the detection section;
a first cover member comprising an upper surface on which the base is located; and
a second cover member which is configured to be joined to the first cover member and is configured to cover the base,
wherein at least one of the first cover member and the second cover member comprises an inflow port through which the analyte flows, and a groove portion extending from the inflow port to the detection section, wherein the second substance further includes a nano particle which is positioned further away from the base than the bond, and wherein the nano particle has a particle size of 100 nanometers or less.

2. The sensor according to claim 1, wherein the amino acid is Arg (arginine).

3. The sensor according to claim 1, wherein the first compound includes a benzene ring.

4. The sensor according to claim 1, wherein the first group of the first compound in the second substance includes at least one of an amino group and a carboxyl group.

5. The sensor according to claim 1, wherein the second substance includes a second compound including a second group capable of bonding to other substances, the second compound being positioned opposite to the first compound with respect to the amino acid.

6. The sensor according to claim 1,
wherein the second substance is represented by a following Expression (1), A-B-amino acid-C-D,     Expression (1)

wherein, each of the A and the D includes at least one selected from a group consisting of Cys (cysteine), Lys (lysine), and biotin and polyethylene glycol derivatives, the B includes at least one selected from a group consisting of amino acids including Pro (proline) and Phe (phenylalanine) and a pipecolic acid, and the C includes an aromatic compound including phenylenediamine and aminobenzoic acid.

7. The sensor according to claim 6, wherein the C of the second substance in the Expression (1) is pPDA (p-phenylenediamine).

8. The sensor according to claim 6, wherein the B of the second substance in the Expression (1) is D-Phe-Pip,
wherein, the D-Phe represents phenylalanine of a D form, and the Pip represents a pipecolic acid.

9. The sensor according to claim 1, wherein the enzyme includes thrombin.

10. The sensor according to claim 1, wherein the first substance includes prothrombin.

11. The sensor according to claim 1, wherein the detection section is capable of measuring a prothrombin time.

12. The sensor according to claim 11, wherein a magnitude of each of blood clotting factors II, V, VII, and X is determined by the prothrombin time.

13. The sensor according to claim 12, wherein the third substance in measuring a prothrombin time is configured to alter into a substance capable of chemically reacting with the blood clotting factor X by reacting chemically with the blood clotting factor VII.

14. The sensor according to claim 1,
wherein the first cover member comprises a recessed portion in the upper surface, the recessed portion being configured to accommodate the base, and
the second cover member comprises the groove portion.

15. The sensor according to claim 1, further comprising the third substance attached to the groove portion.

* * * * *